US00PP36125P2

(12) United States Plant Patent
Kobayashi

(10) Patent No.: US PP36,125 P2
(45) Date of Patent: Sep. 17, 2024

(54) **NEW GUINEA *IMPATIENS* PLANT NAMED 'Dongipetresta'**

(50) Latin Name: *Impatiens hawkeri*
Varietal Denomination: Dongipetresta

(71) Applicant: DUMMEN GROUP B.V., De Lier (NL)

(72) Inventor: Ruth Kobayashi, Carlsbad, CA (US)

(73) Assignee: DUNNEB GROUP B.V., De Lier (NL)

( * ) Notice: Subject to any disclaimer, the term of this patent is extended or adjusted under 35 U.S.C. 154(b) by 0 days.

(21) Appl. No.: 18/526,926

(22) Filed: Dec. 1, 2023

(51) Int. Cl.
*A01H 5/02* (2018.01)
*A01H 6/16* (2018.01)

(52) U.S. Cl.
USPC ..... Plt./318.1

(58) Field of Classification Search
USPC ..... Plt./263.1, 317, 318.12
See application file for complete search history.

(56) References Cited

U.S. PATENT DOCUMENTS

PP34,447 P2 * 7/2022 Kobayashi ..... A01H 6/165 Plt./318.1

* cited by examiner

*Primary Examiner* — Karen M Redden
(74) *Attorney, Agent, or Firm* — C. Anne Whealy

(57) ABSTRACT

A new and distinct cultivar of *Impatiens* plant named 'Dongipetresta' characterized by its upright to outwardly spreading and mounding plant habit; moderately vigorous to vigorous growth habit; freely branching habit; dense and full appearance; dark red-colored leaves; freely and early flowering habit; medium to large-sized single-type white to light pink and red bicolored flowers; and good garden performance.

2 Drawing Sheets

Figure 1:
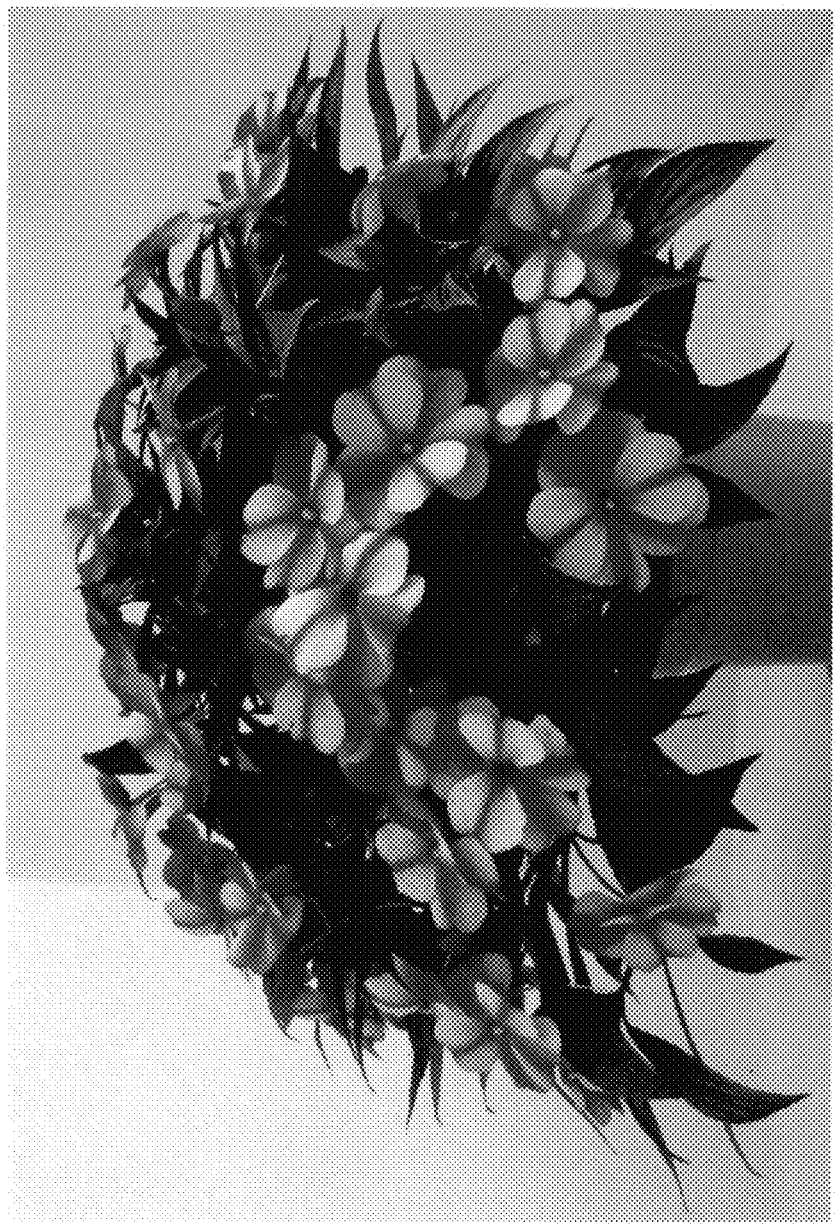

Botanical designation: *Impatiens hawkeri.*
Cultivar denomination: 'DONGIPETRESTA'.

STATEMENT REGARDING PRIOR DISCLOSURES BY INVENTOR & APPLICANT/ASSIGNEE

The Inventor and Applicant/Assignee assert that no sales, offers for sale or public distribution of the instant plant occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of New Guinea *Impatiens* plant, botanically known as *Impatiens hawkeri* and hereinafter referred to by the name 'Dongipetresta'.

The new *Impatiens* plant is a product of a planned breeding program conducted by the Inventor in Koka, Ethiopia and Encinitas, California. The objective of the breeding program is to create new freely-branching, early and freely flowering New Guinea *Impatiens* plants with large attractive flowers and good garden performance.

The new *Impatiens* plant originated from a cross-pollination made by the Inventor in November, 2018 in Koka, Ethiopia of a proprietary selection of *Impatiens hawkeri* identified as code number NN16-596500-001, not patented, as the female, or seed, parent with *Impatiens hawkeri* 'Tamar Purple Bicolor', disclosed in U.S. Plant Pat. No. 15,462, as the male, or pollen, parent. The new *Impatiens* plant was discovered and selected by the Inventor as a single flowering plant from within the progeny of the stated cross-pollination in a controlled greenhouse environment in Encinitas, California in April, 2019.

Asexual reproduction of the new *Impatiens* plant by terminal vegetative cuttings in a controlled greenhouse environment in Encinitas, California since June, 2019 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongipetresta'. These characteristics in combination distinguish 'Dongipetresta' as a new and distinct *Impatiens* plant:

1. Upright to outwardly spreading and mounding plant habit.
2. Moderately vigorous to vigorous growth habit.
3. Freely branching habit; dense and full appearance.
4. Dark red-colored leaves.
5. Freely and early flowering habit.
6. Medium to large-sized single-type white to light pink and red bicolored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more upright than plants of the female parent selection.
2. Plants of the new *Impatiens* are more vigorous than plants of the female parent selection.
3. Plants of the new *Impatiens* have larger flowers than plants of the female parent selection.
4. Flowers of plants of the new *Impatiens* are light pink to white and red bicolored whereas flowers of plants of the female parent selection are dark lavender and burgundy bicolored.

Plants of the new *Impatiens* can be compared to plants of the male parent, 'Tamar Purple Bicolor'. Plants of the new *Impatiens* differ primarily from plants of 'Tamar Purple Bicolor' in the following characteristics:

1. Plants of the new *Impatiens* are more upright than plants of 'Tamar Purple Bicolor'.
2. Plants of the new *Impatiens* flower about one week earlier than plants of 'Tamar Purple Bicolor'.
3. Flowers of plants of the new *Impatiens* are light pink to white and red bicolored whereas flowers of plants of 'Tamar Purple Bicolor' are red purple and lavender bicolored.

Plants of the new *Impatiens* can be compared to plants of *Impatiens hawkeri* 'Duepetrest', disclosed in U.S. Plant Pat. No. 11,375. In side-by-side comparisons, plants of the new *Impatiens* differ primarily from plants of 'Duepetrest' in the following characteristics:

1. Plants of the new *Impatiens* have more upright than plants of 'Duepetrest'.
2. Plants of the new *Impatiens* are more vigorous than plants of 'Duepetrest'.
3. Plants of the new *Impatiens* have larger flowers than plants of 'Duepetrest'.
4. Flowers of plants of the new *Impatiens* are light pink to white and red bicolored whereas flowers of plants of 'Duepetrest' are soft red and light lavender bicolored.

Plants of the new *Impatiens* can also be compared to plants of *Impatiens hawkeri* 'Dueptbus14', disclosed in U.S. Plant Pat. No. 26,780. In side-by-side comparisons, plants of the new *Impatiens* differ primarily from plants of 'Dueptbus14' in the following characteristics:

1. Plants of the new *Impatiens* are not as vigorous as plants of 'Dueptbus14s'.
2. Plants of the new *Impatiens* have larger flowers than plants of 'Dueptbus14'.
3. Flowers of plants of the new *Impatiens* are light pink to white and red bicolored whereas flowers of plants of 'Dueptbus14' are bright red and red purple bicolored.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongipetresta' grown in a container.

Figure 2:
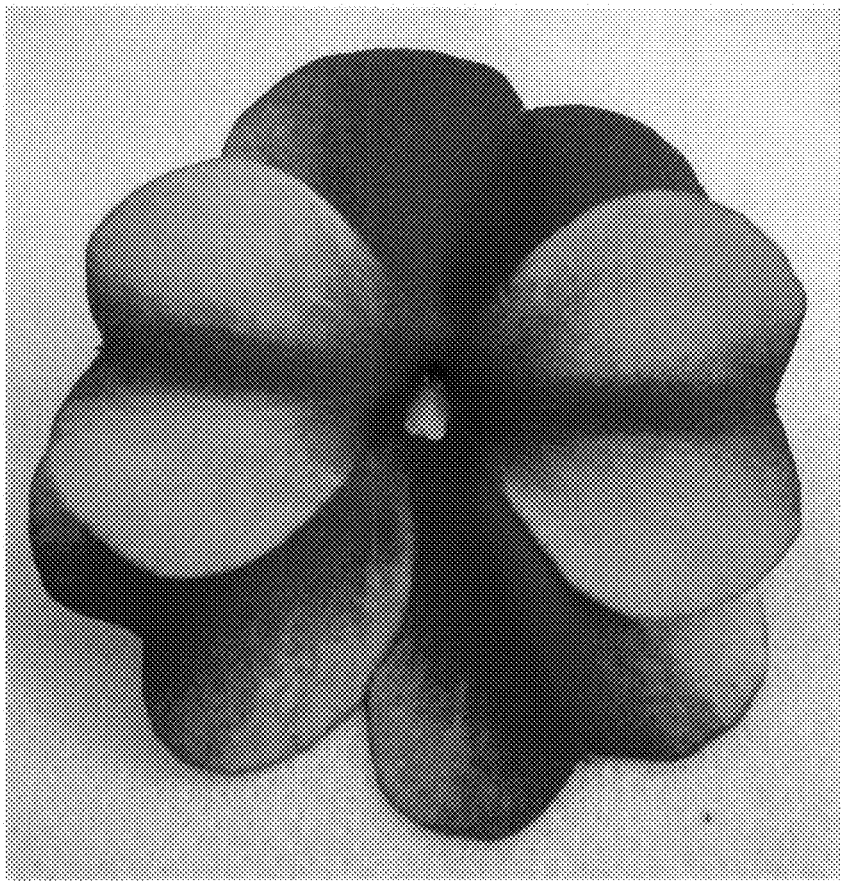

The photograph on the second sheet (FIG. 2) is a close-up view of a typical flower of 'Dongipetresta'.

DETAILED BOTANICAL DESCRIPTION

The aforementioned photographs and following observations, measurements and values describe plants grown during the summer in 16.5-cm containers in a polyethylene-covered greenhouse in Encinitas, California and under cultural practices typical of commercial New Guinea *Impatiens* production. During the production of the plants, day temperatures averaged 25 C, night temperatures averaged 18 C and light levels ranged from 4,000 to 4,500 lux. Plants were 16 weeks old when the photographs were taken and 17 weeks old when the description was taken. In the following description, color references are made to The Royal Horticultural Society Colour Chart, 2015 Edition, except where general terms of ordinary dictionary significance are used.

Botanical classification: *Impatiens hawkeri* 'Dongipetresta'.

Parentage:

*Female, or seed, parent.*—Proprietary selection of *Impatiens hawkeri* identified as code number NN16-596500-001, not patented.

*Male, or pollen, parent.*—*Impatiens hawkeri* 'Tamar Purple Bicolor' disclosed in U.S. Plant Pat. No. 15,462.

Propagation:

*Type.*—By terminal vegetative cuttings.

*Time to initiate roots, summer and winter.*—About five to seven days at temperatures about 27 C and night temperatures about 20 C.

*Time to produce a rooted young plant, summer and winter.*—About three weeks at day temperatures about 27 C and night temperatures about 20 C.

*Root description.*—Fine, fibrous; typically white in color, actual color of the roots is dependent on substrate composition, water quality, fertilizers, substrate temperature and age of roots.

*Rooting habit.*—Freely branching; dense.

Plant description:

*Plant and growth habit.*—Upright to outwardly spreading and mounding plant habit; broad inverted triangle in overall shape; freely branching habit with lateral branches potentially developing at every node; dense and full appearance; moderately vigorous to vigorous growth habit and rapid growth rate.

*Plant height.*—About 30 cm to 33 cm.

*Plant diameter.*—About 56 cm to 61 cm.

Lateral branch description:

*Length.*—About 25.5 cm.

*Diameter.*—About 8 mm to 10 mm.

*Internode length.*—About 5.3 cm to 5.9 cm.

*Strength.*—Strong; flexible.

*Aspect.*—Initially upright to outwardly spreading.

*Texture and luster.*—Smooth, glabrous; glossy.

*Color, developing.*—Close to 146A heavily overlain with close to 187A.

*Color, developed.*—Close to 146A variably overlain with close to 183A and 187A.

Leaf description:

*Arrangement.*—Typically alternate or in whorls; simple.

*Length.*—About 8.5 cm to 10 cm.

*Width.*—About 3 cm to 3.75 cm.

*Shape.*—Elliptic.

*Apex*.—Acuminate.

*Base*.—Cuneate with attenuate tendencies.

*Margin*.—Serrate with ciliation.

*Texture and luster, upper surface*.—Smooth, glabrous; glossy.

*Texture and luster, lower surface*.—Smooth, glabrous; moderately glossy.

*Venation pattern*.—Pinnate; arcuate.

*Color*.—Developing leaves, upper surface: Close to N189A tinged with close to 187A. Developing leaves, lower surface: Close to 187A. Fully expanded leaves, upper surface: Close to between 187A and N186A; venation, close to 187B. Fully expanded leaves, lower surface: Close to 187A; venation, close to 187A.

*Petiole length*.—About 3.5 cm to 4.2 cm.

*Petiole diameter*.—About 3 mm to 3.5 mm.

*Petiole texture and luster, upper and lower surfaces*.—Smooth, glabrous; moderately glossy.

*Petiole color, upper and lower surfaces*.—Close to 59A.

Flower description:

*Flower type and flowering habit*.—Single-type, medium-sized rounded to slightly rectangular axillary flowers; freely flowering habit, typically about four to six flower buds and open flowers per lateral branch; flowers positioned just above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about eleven weeks after planting.

*Flower buds, before showing petal color*.—Length: About 9 mm. Diameter: About 7.5 mm. Shape: Ovoid. Texture and luster: Smooth, glabrous; moderately glossy. Color: Close to 183A.

*Flower diameter*.—About 5.5 cm by 5.75 cm.

*Flower depth*.—About 1.5 cm to 1.75 cm.

*Petals*.—Quantity and arrangement: Five per flower in a single whorl. Length, banner petals: About 2.7 cm. Length, lateral petals: About 2.6 cm. Length, lower petals: About 3.2 cm. Width, banner petal: About 3.6 cm. Width, lateral petals: About 3 cm. Width, lower petals: About 3.2 cm. Shape, all petals: Broadly cordate to obcordate. Apex, all petals: Emarginate. Base, all petals: Cuneate. Margin, all petals: Entire; not undulate. Texture and luster, all petals, upper surface: Smooth, glabrous; velvety; slightly glossy; iridescent. Texture and luster, all petals, lower surface: Smooth, glabrous; slightly glossy. Color, all petals: When opening and fully opened, upper surface: Ground color, close to NN155C variably tinged with close to 65D; star-shaped pattern, close to 53A to 53B, banner petal, may be mostly 53A to 53B; at the throat, close to N57A; venation, similar to lamina colors; colors do not change with subsequent development. When opening and fully opened, lower surface: Close to 65B to 65C variably tinged with close to 53B to 53C, most heavily tinged towards and at the center of the petal; venation, similar to lamina colors; colors do not change with subsequent development.

*Sepals*.—Quantity and arrangement: Three in a single whorl; one modified into an elongated spur. Lateral sepal length: About 9 mm. Lateral sepal width: About 4.5 mm. Spur sepal length: About 1.4 cm. Spur sepal width: About 1 cm. Lateral sepals shape: Ovate. Spur sepal shape: Broadly ovate. Sepal apex, all sepals: Acuminate. Sepal base, all sepals: Truncate. Sepal margin, all sepals: Entire. Sepal texture and luster, all sepals, upper and lower surfaces: Smooth, glabrous; slightly glossy. Lateral sepals color, upper surface: Close to 184A. Lateral sepals color, lower surface: Close to 183A. Spur sepal color, upper surface: Close to 62A. Spur sepal color, lower surface: Close to 60B. Spur length: About 3.3 cm. Spur diameter: At flower, about 3.5 mm; at apex, less than 1 mm. Spur shape: Acicular. Spur texture and luster: Smooth, glabrous; moderately glossy. Spur color: Close to 62A to 62B.

*Peduncles*.—Length: About 3.6 cm to 4 cm. Diameter: About 2 mm. Angle: About 45 degrees from stem axis. Strength: Strong; flexible. Texture and luster: Smooth, glabrous; somewhat glossy. Color: Close to 144A to 144B.

*Reproductive organs*.—Stamens: Quantity: Five fused at anthers; filaments free. Anther size: About 1 mm by 5 mm. Anther shape: Oblong. Anther color: Close to N155B. Pollen amount: None observed. Pistils: Quantity per flower: One. Pistil length: About 2.25 mm. Stigma shape: Crested. Stigma color: Close to 144A. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5 C to about 40 C.

It is claimed:

1. A new and distinct *Impatiens* plant named 'Dongipetresta' as illustrated and described.

* * * * *